(12) United States Patent
Lee et al.

(10) Patent No.: US 7,740,636 B2
(45) Date of Patent: Jun. 22, 2010

(54) MULTI-ACTION DEVICE FOR INSERTING AN INTRAOCULAR LENS INTO AN EYE

(75) Inventors: Ngee Jenn Lee, Chicago, IL (US); Tomas Matusaitis, Chicago, IL (US)

(73) Assignee: Abbott Medical Optics Inc., Santa Ana, CA (US)

( * ) Notice: Subject to any disclaimer, the term of this patent is extended or adjusted under 35 U.S.C. 154(b) by 709 days.

(21) Appl. No.: 11/107,057

(22) Filed: Apr. 15, 2005

(65) Prior Publication Data
US 2006/0235429 A1    Oct. 19, 2006

(51) Int. Cl.
*A61F 9/00*    (2006.01)
*A61F 2/16*    (2006.01)

(52) U.S. Cl. ...................................... 606/107
(58) Field of Classification Search ................. 606/107; 623/6.12; 604/181, 187, 208–210, 110, 57, 604/59–64, 220–222, 224
See application file for complete search history.

(56) References Cited

U.S. PATENT DOCUMENTS

| | | | |
|---|---|---|---|
| 3,452,740 A | | 7/1969 | Muller |
| 4,862,885 A | | 9/1989 | Cumming |
| 4,919,130 A | | 4/1990 | Stoy et al. |
| 4,934,363 A | | 6/1990 | Smith et al. |
| 5,578,042 A | | 11/1996 | Cumming |
| 5,582,614 A | | 12/1996 | Feingold |
| 5,643,275 A | * | 7/1997 | Blake .......................... 606/107 |
| 5,683,116 A | * | 11/1997 | Folkers ......................... 285/18 |
| 5,868,751 A | | 2/1999 | Feingold |
| 5,873,879 A | | 2/1999 | Figueroa et al. |
| 5,891,153 A | | 4/1999 | Peterson |
| 6,143,021 A | | 11/2000 | Staehle |
| 6,214,015 B1 | | 4/2001 | Reich et al. |
| 6,220,859 B1 | | 4/2001 | Hoffman |
| 6,241,737 B1 | | 6/2001 | Feingold |
| 6,251,114 B1 | | 6/2001 | Farmer et al. |
| 6,398,788 B1 | | 6/2002 | Makker et al. |
| 6,666,871 B2 | | 12/2003 | Kikuchi |

(Continued)

FOREIGN PATENT DOCUMENTS

EP    363213 A2    12/1990

(Continued)

*Primary Examiner*—(Jackie) Tan-Uyen T Ho
*Assistant Examiner*—Dianne Dornbusch

(57) ABSTRACT

A device for inserting an intraocular lens (IOL) into an eye includes a tubular body member with an inner surface and a plunger with an gripping device that is receivable within the body member. The gripping device includes a locking member and is configured such that when urged longitudinally in a distal direction, the gripping device is movable in the distal direction within the body member. However, when urged longitudinally in a proximal direction, the gripping device is prevented from moving in the proximal direction by the locking member engaging with the inner surface of the body member. As such, inadvertent movement of the plunger in the proximal direction caused by pulling back on the plunger is substantially prevented. If proximal movement of the plunger is desired, then the plunger may include handle that is operatively coupled to the gripping device such rotation of the handle causes the handle to move longitudinally in the body member. Accordingly, the plunger may be advanced or moved distally by longitudinally pushing the handle and/or by rotating the handle.

7 Claims, 6 Drawing Sheets

U.S. PATENT DOCUMENTS

| | | |
|---|---|---|
| 2003/0040755 A1 | 2/2003 | Meyer |
| 2003/0167060 A1 | 9/2003 | Buzzard et al. |
| 2003/0216745 A1 | 11/2003 | Brady et al. |
| 2004/0059343 A1 * | 3/2004 | Shearer et al. .............. 606/107 |
| 2004/0193180 A1 | 9/2004 | Buzzard et al. |

FOREIGN PATENT DOCUMENTS

| | | |
|---|---|---|
| EP | 1 415 619 A2 | 5/2004 |
| EP | 1 424 048 A1 | 6/2004 |
| EP | 1481652 A1 | 12/2004 |
| EP | 1491163 A2 | 1/2005 |
| WO | WO 96/28121 | 9/1996 |
| WO | WO 2004/105648 A1 | 12/2004 |

* cited by examiner

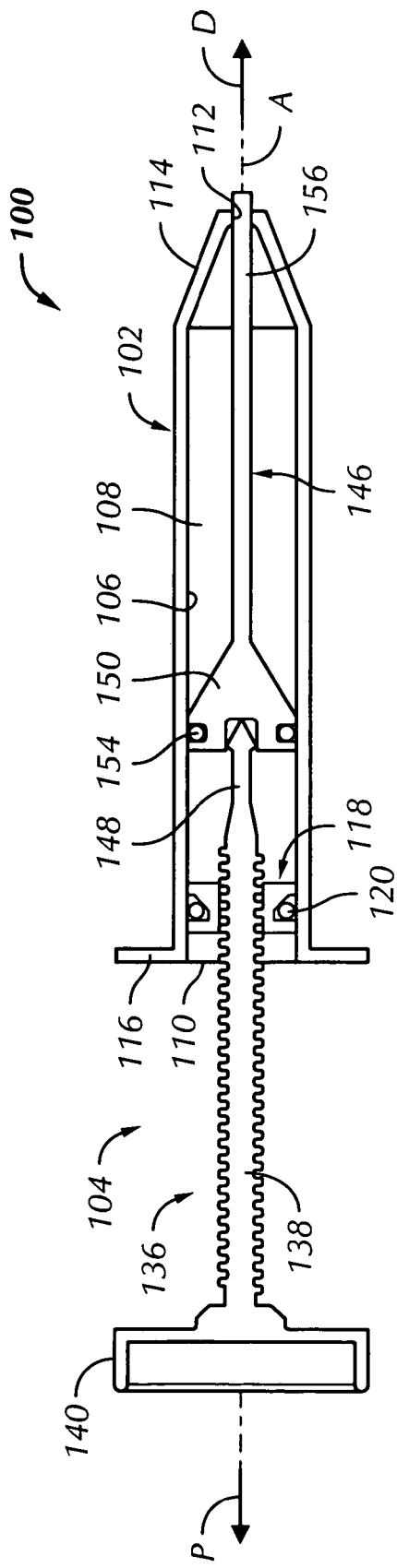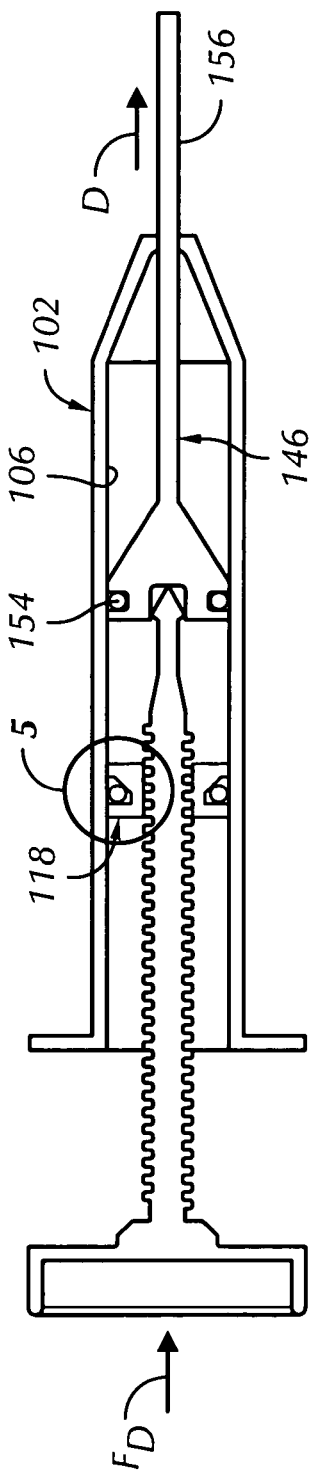
FIG. 2
FIG. 3

MULTI-ACTION DEVICE FOR INSERTING AN INTRAOCULAR LENS INTO AN EYE

BACKGROUND OF THE INVENTION

The present invention relates to apparatus and methodology for inserting an intraocular lens (IOL) into an eye.

The human eye is susceptible to numerous disorders and diseases, a number of which attack the crystalline lens. For example, cataracts mar vision through cloudy or opaque discoloration of the lens of the eye. Cataracts often result in partial or complete blindness. A damaged crystalline lens can be removed and replaced with an intraocular lens, or IOL.

An IOL is implanted in the eye, e.g., as a replacement for the natural crystalline lens after cataract surgery or to alter the optical properties (i.e., provide vision correction) of an eye in which the natural lens remains. IOLs often include a disk-like optic that is optically clear. Many IOLs also include at least one flexible fixation member or haptic which extends radially outward from the optic and becomes affixed in the eye to secure the lens in position. Implantation of IOLs into the eye involves making an incision in the eye. To reduce trauma and to speed healing, it is advantageous to minimize the size of the incision.

The optics may be constructed of rigid biocompatible materials such as polymethyl methacrylate (PMMA) or deformable materials such as silicone polymeric materials, acrylic polymeric materials, hydrogel polymeric materials, and the like. Deformable materials allow the IOL to be rolled or folded for insertion through a small incision into the eye. A substantial number of instruments have been proposed to aid in inserting such a foldable lens in the eye.

The two primary IOL materials are silicone and acrylic. Silicone IOLs are more pliable and can be folded into smaller tubes without unduly stressing the insertion cartridge, or requiring excessive push force which can violently expel the IOL from the cartridge. Acrylic lenses are indicated for some patients and are inserted in much the same way as silicone IOLs, although using larger bore cartridges to mitigate the problems caused by the lower flexibility of the acrylic. Because the cartridge bore is larger, the incision is also necessarily larger.

In view of the foregoing, there is a continued need in the art for beneficial advancements in IOL insertion apparatus and methodology.

SUMMARY OF THE INVENTION

According to one aspect of the invention, a device for inserting an intraocular lens (IOL) into an eye includes a tubular body member with an inner surface and a plunger with a gripping device that is preferably annular in form and is receivable within the body member. The gripping device includes a locking member and is configured such that when urged longitudinally in a distal direction, the gripping device is movable in the distal direction within the body member. However, when urged longitudinally in a proximal direction, the gripping device is prevented from moving in the proximal direction by the locking member engaging with the inner surface of the body member.

One of the advantages of the device is that inadvertent movement of the plunger in the proximal direction caused by pulling back on the plunger, movement that may be unwanted during a surgical procedure, is substantially prevented. If proximal movement of the plunger is desired, then according to another aspect of the invention, the plunger may include a handle that is operatively coupled to the gripping device such that rotation of the handle causes the handle to move longitudinally in the body member. Accordingly, the plunger may be advanced or moved distally by longitudinally pushing the handle and/or by rotating the handle, while the plunger may be moved proximally only by rotating the handle.

Another one of the advantages is that the locking member may be configured as a seal member, such as an O ring or another element that is capable of forming a sealing between two components. More specifically, when the gripping device is moving in the distal direction, the locking member forms a seal between the gripping device and the inner surface of the body member. The seal also enhances smooth distal movement of the gripping device.

According to another aspect of the invention, the gripping device may include a collar with a circumferential seat for receiving the locking member. The seat may include a proximally disposed channel and a distally disposed wedge such that when the collar is urged distally, the locking member is received in the channel, thereby allow distal movement, and when the collar is urged proximally, the locking member is urged between the wedge and the inner surface of the body member, thereby impeding or preventing proximal movement. In these embodiments, the locking member may be, for example, an O ring, a slit O ring, a set of spherical or elongated balls, or a plurality of substantially cylindrical sections. In certain embodiments, the locking member may additionally act as a seal. In yet other embodiments, the locking member may include a plurality of pliable baffles that allow the gripping device to move distally but that impede proximal movement of the gripping device.

Other features and advantages of the present invention will become apparent to those skilled in the art from a consideration of the following detailed description taken in conjunction with the accompanying drawings.

BRIEF DESCRIPTION OF THE SEVERAL VIEWS OF THE DRAWINGS

FIG. 2 is a cross-sectional view of the device with a plunger in an initial position in a body member;

FIG. 3 is a view similar to FIG. 2 with the plunger moving in a distal direction;

DETAILED DESCRIPTION OF THE INVENTION

Figure 1:
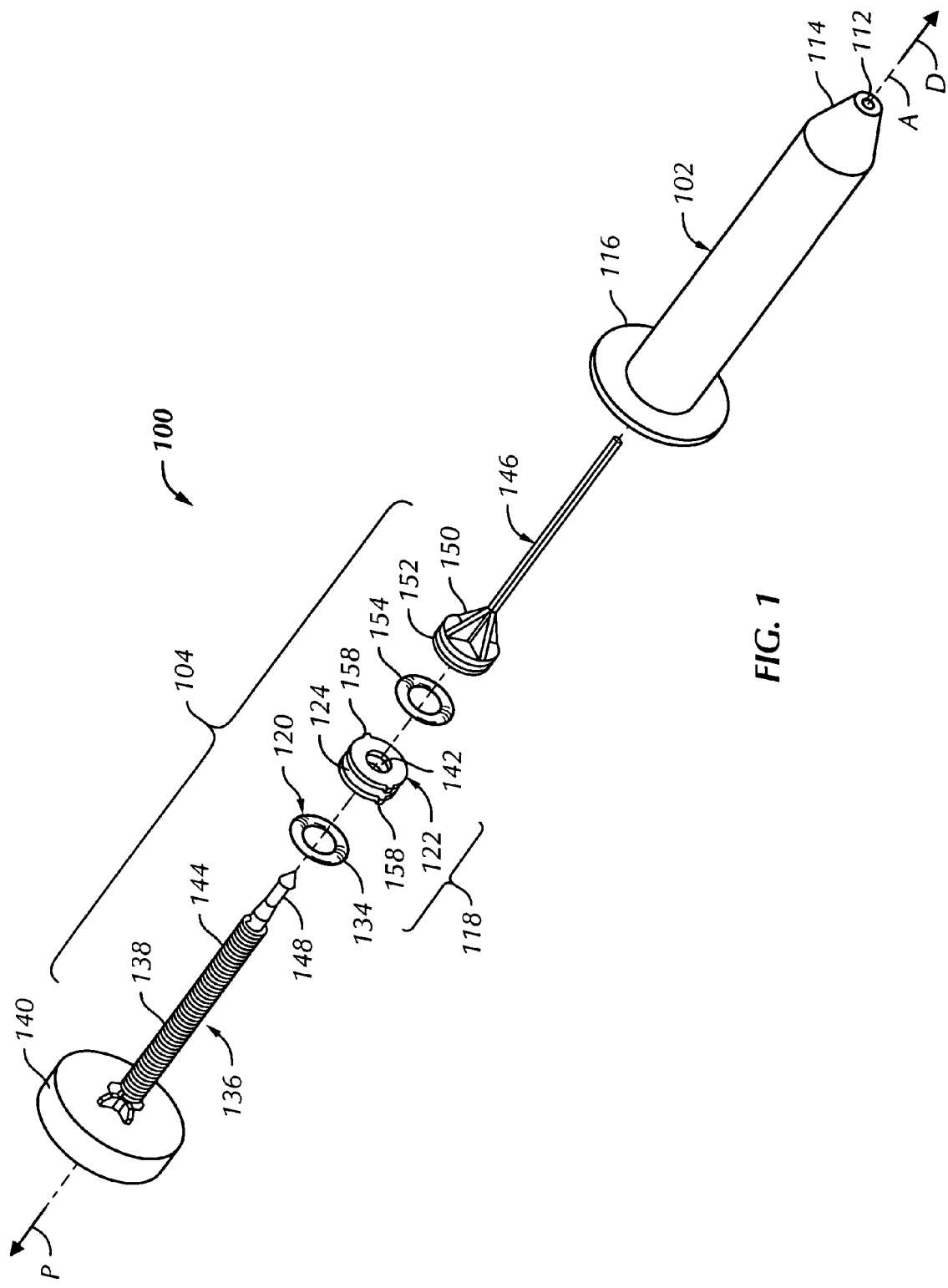
FIG. 1 is an exploded perspective view of a device for inserting an intraocular lens (IOL) into an eye according to a number of embodiments.

Referring to FIG. 1, a device 100 for inserting an intraocular lens (IOL) into an eye includes a body member 102. In a number of embodiments, the device 100 may be described as also including a plunger 104. Depending upon a particular embodiment, the device 100 may be configured so that the plunger 104 is slidable in the body member 102 in only one direction, namely, a distal direction, but not in the opposite proximal direction. Additionally or alternatively, the device may be configured so that the plunger 104 is moveable in the distal direction through rotation. This rotation may be in conjunction with or separate from the sliding motion of the plunger 104.

Describing a number of embodiments in more detail such as shown in FIGS. 1 and 2, the body member 102 may be substantially tubular with an inner surface 106 defining an inner through chamber 108. The body member 102 may also be described as having a proximal entry 110 and a distal port 112, with a longitudinal axis A and a distal direction D and a proximal direction P. In some of the embodiments, the body member 102 may include a distal portion 114 that is generally frustum shaped and an annular flange 116 disposed at or near the proximal opening 110.

In certain embodiments, the device 100 may further comprise a cartridge (not shown) for holding an intraocular lens. In such embodiments, the cartridge is preferably attached in the vicinity of the distal portion 114 of the device 100, in which case the distal portion 114 may have a configuration other than the generally frustum shape shown in FIG. 1. In certain embodiments, the cartridge may be preloaded with the intraocular lens and/or pre-mounted onto the device 100 prior to shipment to a practitioner or other user.

With continued reference to FIGS. 1 and 2, the plunger 104 may be configured according to a number of embodiments. For example, in some of the embodiments the plunger 104 may include a directionally biasing or gripping device 118 with a locking member 120. In many embodiments, the locking member 120 may be disposed circumferentially about the gripping device 118. The gripping device gripping device 118 is receivable within the body member 102 as particularly shown in FIG. 2.

For the purposes of this description, the gripping device 118 may include any element or structure that provides a support or a purchase for another device or element. In addition, the gripping device may also include any device that is applied mechanically to move something or to prevent something from slipping, or that is utilized to obtain a mechanical advantage. According to principles of the invention, the gripping device 118 need not be a stationary or immobile device but rather is moveable or positionable as desired within the body member 102.

Figure 4:
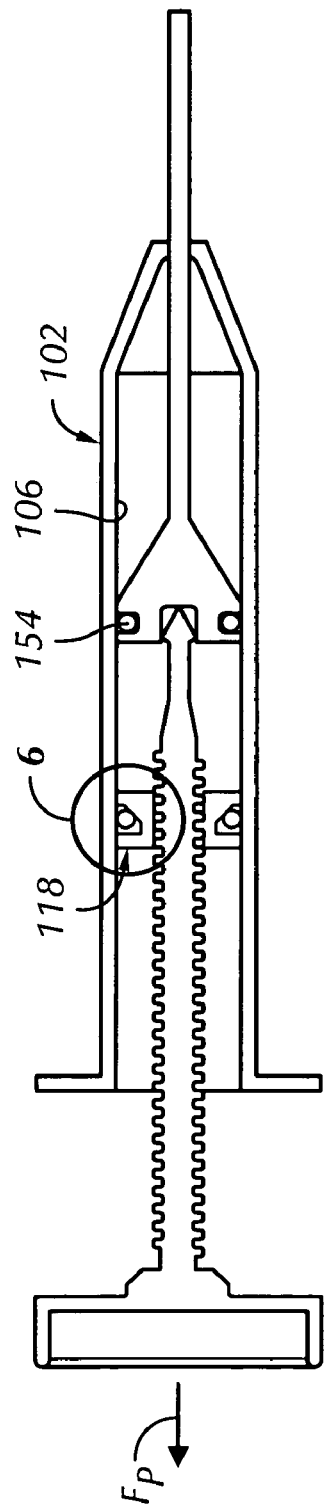
FIG. 4 is a view similar to FIG. 3 with the plunger being urged in a proximal direction.

More specifically, according to some of the embodiments, the gripping device 118 is configured so that when urged longitudinally in a first direction, e.g., the distal direction D as shown by arrow $F_D$ illustrated in FIG. 3, the gripping device 118 is movable in the first direction within the body member 102, as illustrated by arrow D. The gripping device 118 is further configured so that when urged longitudinally in a second direction that is opposite to the first direction, e.g., the proximal direction P as shown by arrow $F_P$ in FIG. 4, the gripping device 118 is impeded or substantially prevented from moving in the second direction by the locking member 120 engaging with the inner surface 106 of the body member 102, which is described in more detail below. Accordingly, the locking member 120 may be described as a unidirectional locking member which is capable of moving in a single longitudinal direction within the body member 102.

According to a number of embodiments, the gripping device 118 may be configured so that when urged in the distal direction D, the locking member 120 slidingly engages with the inner surface 106 of the body member 102. In this regard, the locking member 120 may be configured as a seal member, for example, such as an O ring, either a smooth of continuous O ring or as a ribbed O ring. Accordingly, the sliding engagement between the locking member 120 and the inner surface 106 may also be a sealing engagement as indicated by S in FIG. 5. In these types of embodiments, the inner surface 106 of the body member 102 may be substantially smooth to enhance the sliding engagement of the gripping device 118 and the inner surface 106. The sealing engagement between the gripping or locking member 120 and the inner surface of the body member enhances or ensures smooth, steady, and consistent distal movement of the gripping device 118.

Accordingly, the gripping device 118 is configured to move longitudinally within the body member. Depending upon the particular embodiment, the gripping device 118 may be configured so that the locking member 120 slidingly moves within the body member, wherein such sliding movement may be a translation (i.e., movement without substantial rotation) or may also entail rotation as well. Alternatively, the gripping device 118 may be configured so that the locking member 120 slidably engages the inner surface 106 of the body member 120, wherein such slidable engagement includes contact between the locking member 120 and the body member 102. Still alternatively, the gripping device 118 may be configured so that the locking member 120 sealingly engages the inner surface 106 of the body member 102, wherein such sealing engagement includes a seal between the locking member 120 and the inner surface 106.

Figure 5:
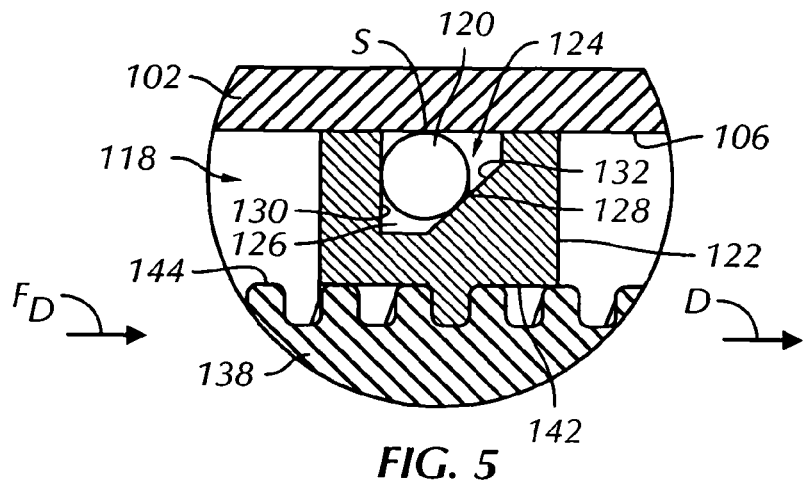
FIG. 5 is an enlarged cross-sectional view taken at circle 5 of FIG. 3.

As also shown in FIG. 5, in some of the embodiments, the gripping device 118 may include a collar 122 with a circumferential seat 124 for receiving the locking member 120. The seat 124 may include a proximally disposed channel 126 and a distally disposed wedge 128. The channel 126 may be defined as having a proximal wall 130. Accordingly, when the collar 122 is urged distally as indicated by arrow $F_D$ in FIG. 5, the locking member 120 is received in the channel 126, abutting the proximal wall 130. And when the collar 122 is urged proximally as indicated by arrow $F_P$ in FIG. 6, the locking member 120 is urged between the wedge 128 and the inner surface 106 of the body member 102, thereby impeding or substantially preventing proximal movement of the collar 122 and, therefore, the gripping device 118.

Figure 6:
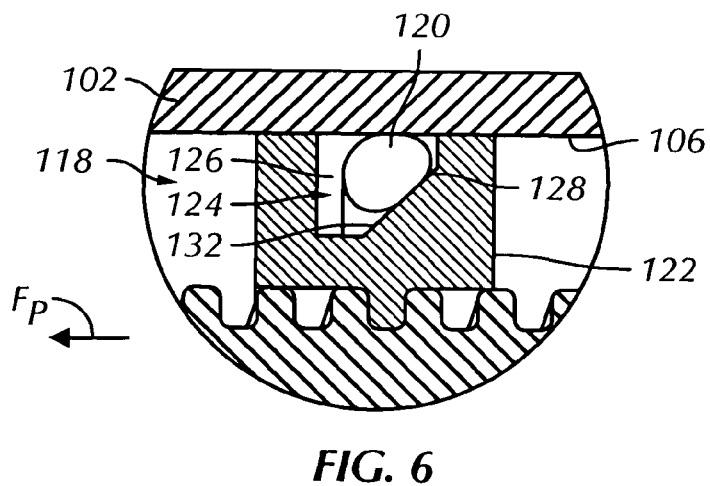
FIG. 6 is a view similar to FIG. 5 taken at circle 6 of FIG. 4.

As particularly shown in FIGS. 5 and 6, the wedge 128 of the seat 124 may be described as an incline surface 132 that may be either straight or arcuate, and the is preferably angles outwardly toward the inner surface 106 and distally toward the distal portion 114 of the body member 102. Accordingly, when the collar 122 is urged distally, the locking member 120 is received in the channel 126 as shown in FIG. 5, and when the collar 122 is urged proximally, the locking member 120 is wedged between the inclined surface 132 and the inner surface 106 of the body member 102 as shown in FIG. 6.

Depending upon the particular embodiment and selected parameters of the individual elements, the seat 124 and the locking member 120 may be configured so that when the locking member 120 is wedged between the inclined surface 132 and the inner surface 106 of the body member 102, proximal movement of the collar 122 is substantially prevented. For example, in a number of embodiments, the locking member 120 may be or may include an O ring 134 as shown in FIG. 1. The O ring 134 may be made from an elastic or resilient material that is compressible under force as shown in FIG. 6. Alternatively, the locking member 120 may be, for example, a slit O ring, a set of spherical or elongated balls, or a plurality of substantially cylindrical sections. In certain embodiments, the locking member 120 additionally acts as a seal.

Depending upon, for example, the coefficient of friction between the O ring 134 and the inner surface 106, the collar 122 may be substantially immoveable in the proximal direction, even under force from a high level of human effort. In other embodiments, the level of force required to move the collar in the proximal direction may essentially destroy the gripping device 118, rendering the device 100 unusable. For example, the force required may crack elements or disconnect the plunger 104. Alternatively, the O ring 134 may have different dimensions to cause the gripping device 118 to tilt under the proximal face, causing the gripping device 118 to become lodged further in the body member 102.

In many embodiments, the plunger 104 may also include a handle 136 with an elongated stem 138 and a knob 140, with the stem 138 being operatively coupled to the gripping device 118. For example, as illustrated in FIGS. 2 and 3, the stem 138 is operatively coupled to the gripping device 118 such that when the handle 136 is urged longitudinally in the distal direction D, the handle 136 and the gripping device 118 move longitudinally in the distal direction D. In other embodiments, the stem 138 may be operatively coupled to the gripping device 118 such that the handle 136 is rotatable with respect to the gripping device 118.

Figure 7:
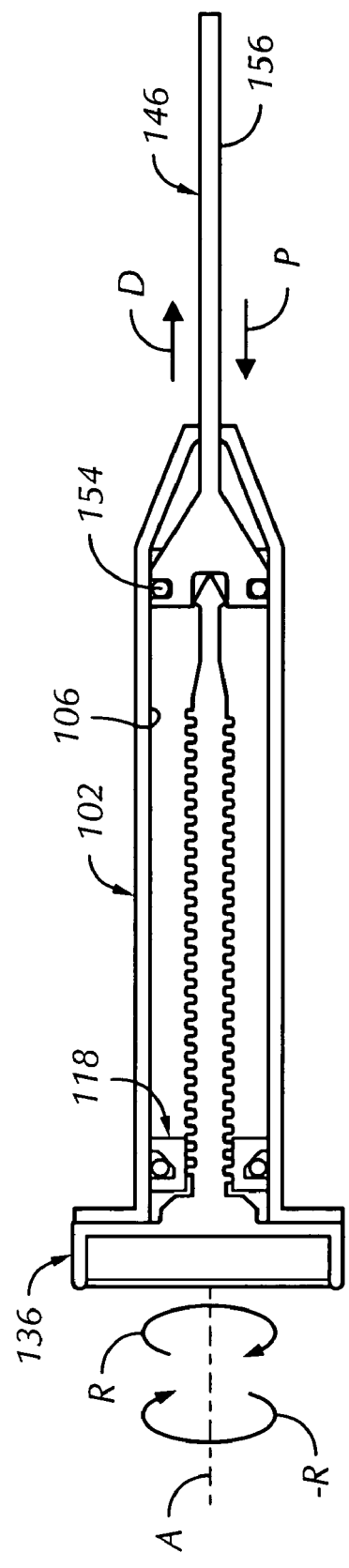
FIG. 7 is a view similar to FIG. 2 with the plunger moving longitudinally due to rotation.

With the gripping device 118 being impeded from moving proximally, the stem 138 may be operatively coupled to the gripping device 118 such that when rotated in a first direction about the longitudinal axis A, as indicated by arrow R in FIG. 7, the handle 136 moves longitudinally in the distal direction D with respect to the gripping device 118. In addition, the stem 138 may be operatively coupled to the gripping device 118 such that when rotated in a second direction about the longitudinal axis A as indicated by arrow-R in FIG. 7, the handle 136 moves longitudinally in the proximal direction P with respect to the gripping device 118.

In rotational embodiments, the collar 122 of the gripping device 118 may include a threaded through hole 142 as shown in FIGS. 1 and 5, and the stem 138 of the handle 136 may include threading 144 disposed along a substantial extent thereof for engaging with the through hole 142. Accordingly, rather than longitudinally urging the handle 136 distally through the body member 102, the handle 136 may be rotated by manipulating the knob 140 to cause the handle 136 to move longitudinally through the body member 102.

In this regard, the plunger 104 may also include an inserter 146 operatively coupled to a distal end 148 of the stem 138 of the handle 136. The inserter 146 may include a base 150 with a circumferential seat 152 for receiving a seal member 154 such as an O ring. In many of the embodiments, the insert 146 and the seal member 154 may be configured to slidably engage the inner surface 106 of the body member 102 as shown in FIGS. 2, 3, 4, and 7. In addition, the inserter 146 may include an elongated distal probe 156 that is slidably receivable through the distal port 112 of the body member 102 as also shown in these same figures.

Figure 8:
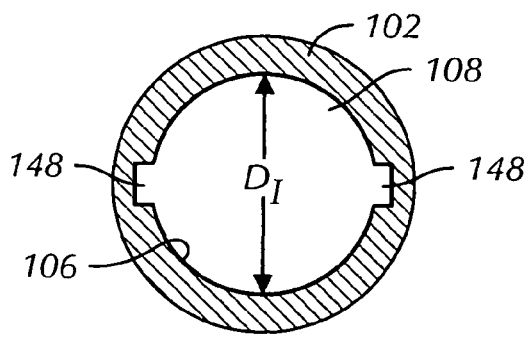
FIG. 8 is a cross-sectional view of a body member according to a number of embodiments.
Figure 9:
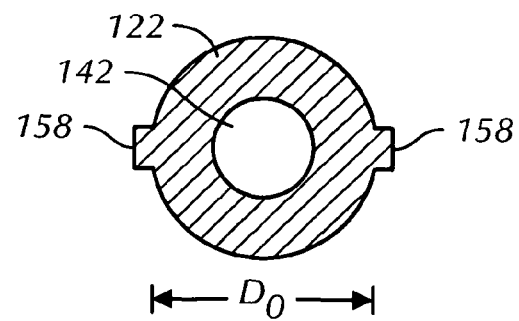
FIG. 9 is a cross-sectional view of a collar according to a number of embodiments.

In a number of embodiments, the device 100 may include structure that prevents the gripping device 118 from rotating with respect to the body member 102. For example, as shown in FIGS. 8 and 9, one or more longitudinal channels 148 may be formed in the inner surface 106 of the body member 102, and complementary bosses 150 (see also FIG. 1) may be disposed on the collar 122 for slidingly engaging with the channels 148. Accordingly, the channels 148 and the bosses 158 prevent any rotation of the collar 122 that may be caused by a rotation of the handle 136.

To enhance the sliding engagement of the gripping device 118 in the body member 102, an outer diameter $D_O$ of the collar 122 may be substantially equal to an inner diameter $D_I$ of the through channel 108 of the body member 102. Accordingly, as shown in, e.g., FIG. 5, the collar 122 slidingly contacts the inner surface 106 of the body member 102.

Figure 10:
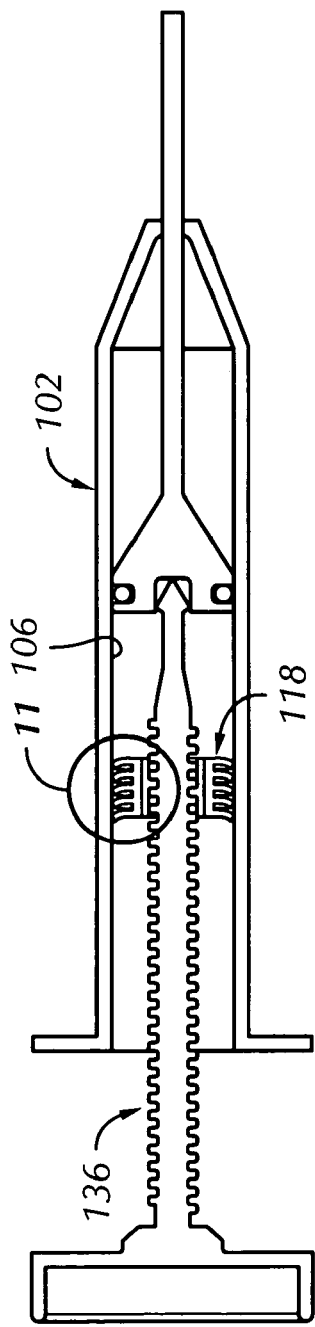
FIG. 10 is a cross-sectional view of a device for inserting an IOL into an eye according to some of the embodiments.
Figure 11:
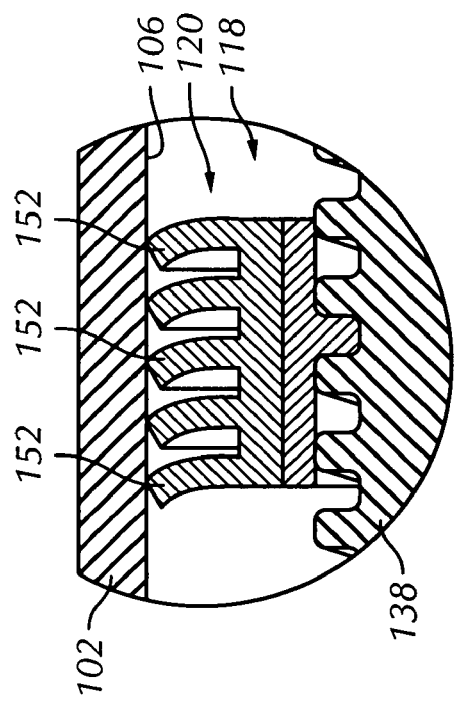
FIG. 11 is an enlarged cross-sectional view taken at line 11 of FIG. 10.
Figure 12:
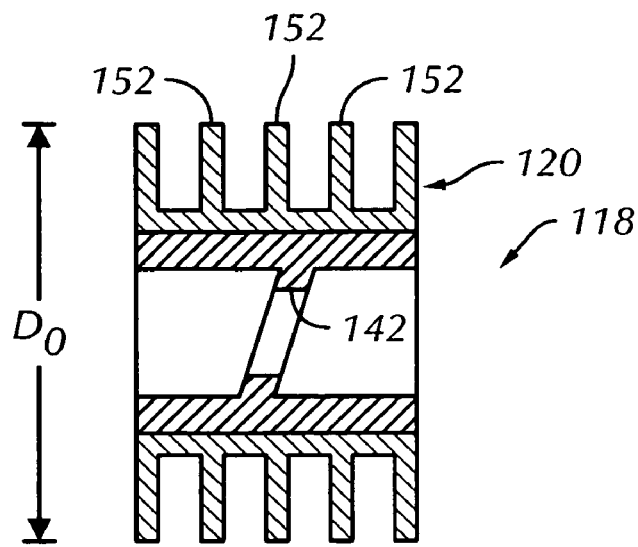
FIG. 12 is a cross-sectional view of a gripping device according to a number of embodiments.

Other embodiments of the gripping device 118 are illustrated in FIGS. 10, 11, and 12 in which locking member 120 includes a plurality of circumferential baffles 152. The baffles 152 are configured to slidingly engage the inner surface 106 of the body member 102 when the gripping device 118 is urged distally and to grippingly engage the inner surface 106 of the body member 102 when the gripping device 118 is urged proximally.

As shown in FIG. 12, the baffles 152 may have an outer diameter $D_O$ that is greater than the inner diameter $D_I$ of the through channel 108 of the body member 102 (see FIG. 8). Accordingly, when inserted through the proximal opening 110 into the through channel 108, the baffles 152 bend and angle proximally as shown in FIGS. 10 and 11. The baffles 152 are, accordingly, biased against the inner surface 106 of the body member 102 to form a slidable locking device therewith when the gripping device 118 moves in the distal direction. Alternatively, the baffles may be fabricated to be prebent to accentuate distal movement more. In certain embodiments, the inner surface 106 may be textured or otherwise formed to enhance gripping action.

Figure 13:
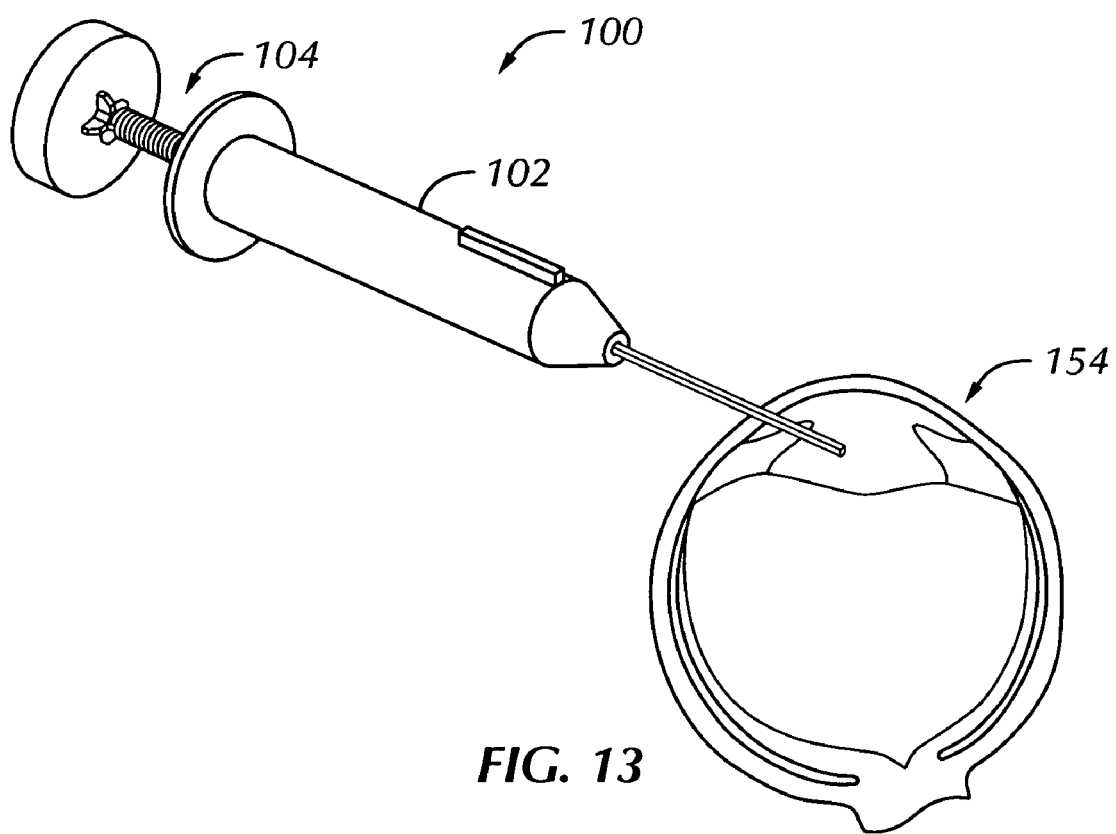
FIG. 13 illustrates the device being used in a surgical procedure of an eye.

In use, as shown in FIG. 13, an IOL may be inserted into an eye 154 with the device 100 by urging the plunger 104 longitudinally and/or rotating the plunger 104 to cause the distal probe 146 to move distally out of the body member 102. The probe 146 may then be positioned in the eye 154 according to known procedures. The plunger 104 may continue to be actuated and/or manipulated as described above. In certain embodiments, the device 100 my further comprise a cartridge (not shown) that contains an intraocular lens. The cartridge may be either preloaded with the intraocular lens prior to shipment or the intraocular lens may be loaded by a practitioner or their assistant during a surgical procedure. The cartridge is preferably disposed around the distal portion 114.

Those skilled in the art will understand that the preceding exemplary embodiments of the present invention provide the foundation for numerous alternatives and modifications thereto. For example, although the drawings illustrate circular embodiments of, e.g., the body member 102 and gripping device 118, other non-circular or non-annular embodiments of the device 100 may be utilized. These and other modifications are also within the scope of the present invention. Accordingly, the present invention is not limited to that precisely as shown and described above but by the scope of the appended claims.

What is claimed is:

1. A method for inserting an intraocular lens (LOL) into an eye, the method comprising:
   providing a device with a body member and a plunger that is slidably received in the body member such that the plunger is slidable in a distal direction and is impeded from sliding in a proximal direction by a gripping device receivable within the body member and including a locking member and a collar with a circumferential seat for receiving the locking member, wherein the locking member is housed within the circumferential seat, wherein the circumferential seat is configured to face an inner surface of the body member, wherein the locking member engages the body member when the plunger is urged in the proximal direction to impede sliding the plunger in the proximal direction while permitting the plunger to slide in the distal direction; and urging the plunger in the distal direction.

2. The method of claim 1 wherein the providing step further comprises providing the device with the body member and the plunger with a handle that is rotatable with respect to the body member such that when the handle is rotated, the plunger moves in at least the distal direction.

3. The method of claim 2 further comprising rotating the handle to cause the plunger to move in the distal direction.

4. The method of claim 2 wherein the providing step further comprises providing the device with the body member and the plunger with the handle that is rotatable with respect to the body member such that when the handle is rotated in a first direction, the plunger moves in the distal direction; and when the handle is rotated in a second direction, the plunger moves in the proximal direction.

5. The method of claim 1, wherein the circumferential seat includes a proximally disposed channel and a distally disposed wedge such that: when the collar is urged distally, the locking member is received in the channel; and when the collar is urged proximally, the locking member is urged between the wedge and the inner surface of the body member, thereby substantially preventing proximal movement.

6. The method of claim 5, wherein the locking member is an O-ring.

7. The method of claim 1, wherein the gripping device further comprises at least one protrusion, wherein the protrusion is coupled to the collar and configured to couple the gripping device with the plunger.

* * * * *